United States Patent [19]

Bacskai

[11] 3,939,201

[45] Feb. 17, 1976

[54] ESTERS

[75] Inventor: Robert Bacskai, Kensington, Calif.

[73] Assignee: Chevron Research Company, San Francisco, Calif.

[22] Filed: Nov. 9, 1973

[21] Appl. No.: 414,584

[52] U.S. Cl. ......... 260/488 J; 260/31.6; 260/410.6; 260/469; 260/475 R; 260/476 R
[51] Int. Cl.$^2$.................. C07C 69/30; C07C 69/78
[58] Field of Search .......... 260/488 J, 476 R, 410.6, 260/469

[56] References Cited
OTHER PUBLICATIONS

Chem. Abstracts, 70:29717 (1969).

Primary Examiner—Vivian Garner
Attorney, Agent, or Firm—G. F. Madgeburger; John Stoner, Jr.; T. G. De Jonghe

[57] ABSTRACT

Triesters of triethanolmethane and a monocarboxylic acid, wherein said acid has from 3 to 15 carbon atoms. The triesters are particularly useful as plasticizers in polyvinyl chloride.

5 Claims, No Drawings

ESTERS

BACKGROUND OF THE INVENTION

The present invention is related to esters, particularly esters useful as plasticizers in polymers such as polyvinyl chloride (PVC).

Plasticizers for use in PVC are described in chapter 5 of H. A. Sarvetnick's book "Polyvinyl Chloride," V. Nostrand Publishing Co., 1969. U.S. Pat. No. 1,929,453 to W. L. Semon is an early patent disclosing the production of rubbery gels by combining an organic solvent, such as an ester, with PVC. Although plasticizers are used in polymers other than PVC, it has been said that PVC applications consume approximately 80% of the total plasticizer production.

In accordance with 1966 statistics as reported in the aforementioned Sarvetnick reference, dioctylphthalates are the most widely used plasticizers for PVC.

Triethanolmethane has been disclosed as a reactant to prepare 1-methylquinuclidinium hydroxide, Chem. Listy, Vol. 50, p. 1624-9 (1956) by R. Luker et al, Univ. of Prague. However, triesters of triethanolmethane do not appear to have been disclosed, nor the use of such triesters in PVC as a plasticizer.

SUMMARY OF THE INVENTION

According to the present invention, a new compound is provided, namely a triester of triethanolmethane and a monocarboxylic acid, wherein said acid has from 3 to 15 carbon atoms.

Generally, the triester can be described by the following formula:

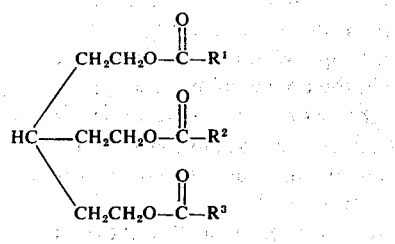

wherein $R^1$, and $R^2$ and $R^3$ are hydrocarbyl groups having from 2 to 14 carbon atoms.

The term "hydrocarbyl" is used herein to mean a hydrocarbon radical with one free bond; that is, a radical composed of hydrogen and carbon as, for example, a butyl radical.

Preferably $R^1$, $R^2$ and $R^3$ are aryl or alkyl groups having from 6 to 8 carbon atoms. I have found that alkyl groups give especially advantageous results as plasticizers, particularly alkyl groups containing from 6 to 8 carbon atoms.

Among other factors, the present invention is based on my finding that triesters of triethanolmethane (TEM) when used as a plasticizer give very good properties to PVC, and furthermore that the triesters of TEM are unexpectedly better as plasticizers in PVC than the corresponding esters of trimethylolpropane (TMP). Still further, I have found that certain triesters of TEM such as triethanolmethanetri-2-ethylhexanoate and triethanolmethanetrihexanoate are unexpectedly superior to dioctylphthalate in resultant flexibility-temperature properties in PVC containing the ester as a plasticizer.

The use of esters in PVC as plasticizers is known in the art. The manner, including the amounts, in which the esters of the present invention are used in PVC is in accordance with conditions so as to effectively use the esters as a plasticizer. Thus, the amount of the ester used in the plasticizer is in general in accordance with typical prior art amounts, and other conditions such as the use of a stabilizer and the like are in accordance with techniques so as to achieve effective plasticizing of the PVC.

The term "plasticizer" is used herein to mean a material incorporated in a plastic to increase its workability and its flexibility. In order for the plasticizer to function, it must be intimately incorporated into the resin (plastic). This is most commonly accomplished by the hot-compounding method of plasticization. In this method the resin and the plasticizer are heated and mixed until a single homogenous phase is obtained. For example, PVC particles and the desired plasticizer are mixed and fluxed together in a Banbury mixer or on a two-roll rubber mill at about 150° to 170°C. Other ingredients such as stabilizers, pigments, fillers, lubricants, etc., may also be included. The mixture first becomes homogenous and then forms a sheet around one roll. This sheet is the plasticized PVC, useful for innumerable applications. The esters of this invention are high-boiling liquids which are readily mixed with PVC powder and then hot-rolled to a final plasticized-PVC product.

Other satisfactory methods of incorporating plasticizers into resins are known. These include: (1) the dry-blending method, wherein the two substances are stirred together for a short time at 50° to 60°C., and then by heating briefly to about 160°C. during further processing the resin becomes plasticized; or (2) the solvent method wherein the resin and the plasticizer are dissolved in a suitable solvent and the plasticized product is recovered by evaporation. Methods of incorporation of plasticizers into resins or plastics are disclosed in "The Encyclopedia of Polymer Science and Technology," Vol. 10 (1969), particularly at p. 228.

Preferred amounts of the triesters of the present invention for use in PVC are between about 3 and 70 weight percent, more preferably between about 20 and 50 weight percent.

Thus, in accordance with the present invention, a new PVC composition is provided, namely PVC containing the triesters of the following formula:

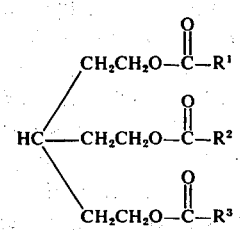

wherein $R^1$, $R^2$ and $R^3$ are hydrocarbyl groups having from 2 to 14 carbon atoms. It is, of course, to be understood that the triester is used in PVC in sufficient amount to be an effective plasticizer.

I have found that especially good plasticizing results are obtained with triethanolmethanetri-2-ethylhexanoate and triethanolmethanetrihexanoate.

Satisfactory acids used to produce the esters of the present invention are monocarboxylic acids having from 3 to 15 carbon atoms. Preferably the acids used to form the triesters of the present invention are hydrocarbon in structure except for the carboxylic group, that is, the acids preferably are composed of hydrogen and carbon except for the oxygen of the carboxylic group. Aliphatic and aromatic monocarboxylic acids are preferred, and saturated aliphatic acids are especially preferred. Preferred acids include propionic, pentanoic, octanoic, decanoic, dodecanoic, 3-methyloctanoic, 4-methylpentanoic, o-ethylbenzoic, p-isopropylbenzoic, m-toluic, mixed amylbenzoic, etc. Mixtures of acids are also satisfactory, thereby giving triesters having more than one kind of acid in the molecule. I have found that particularly preferred acids are those having from 6 to 8 carbon atoms, most preferably the $C_6$–$C_8$ aliphatic monocarboxylic acids.

The triesters of the present invention are readily prepared by esterification procedures known in the art. For example, a mixture of 1 mol of TEM and 3 mols of a monocarboxylic acid is heated to temperatures in excess of 50°C., preferably 90°C., in the presence of a catalytic amount of a mineral acid, e.g., hydrochloric or sulfuric, until about 3 mols of water are evolved and removed through an appropriate condenser. Azeotroping agents, such as benzene, can be added to aid in removing the water of reaction. When esterification is complete, the excess acidic substances are removed by a basic extraction or washing. In general, the triesters are then ready for use. For extreme-purity product, the triester may be distilled, preferably under reduced pressure.

Alternatively, triesters may be prepared by mixing TEM and the desired acid in a molar ratio of about 1:3, and then heating at temperatures in excess of 100°C. to drive off the by-product water. In this case, the crude ester product is generally pure enough for many plasticizing applications.

EXAMPLES

Preparation of triethanolmethanetri-2-ethylhexanoate: A 100-ml, round-bottom flask, equipped with a thermometer and condenser with a Dean-Stark trap, was charged with 15.6 g (0.105 mol) of triethanolmethane, 43.2 g (0.300 mol) of 2-ethylhexanoic acid and 10 g of dibutyl ether. The resulting mixture was heated to the reflux under a nitrogen atmosphere. After 25.5 hours of heating, 0.74 g (0.005 mol of triethanolmethane was added and heating was continued for an additional 41 hours. During this time, 5.35 g (0.298 mol) of water was recovered in the trap. Then the solution was evaporated on a rotary vacuum evaporator at 200°C under about 10 mm pressure. In this way, there was obtained 46.1 g of triethanolmethanetri-2-ethylhexanoate. Analysis, calculated for $C_{31}O_6H_{58}$: C, 70.68%; H, 11.11%. The analysis found experimentally was: C, 69.58%; H, 10.79%. Infrared analysis showed strong adsorption bands at 2940, 1720, 1460, 1380, 1170 and 980 cm.$^{-1}$.

Other triesters were prepared in essentially the same way. These are listed in Table I.

TABLE I

| | Triesters of Triethanolmethane Triester Product | | |
|---|---|---|---|
| Analysis | Hexanoate | Benzoate | Di-2-ethylhexanoate monobenzoate |
| %C, calc. | 67.48 | 73.03 | 71.39 |
| found | 67.59 | 72.80 | 69.86 |
| %H, calc. | 10.48 | 6.31 | 9.59 |
| found | 10.32 | 6.22 | 9.49 |
| Infrared, cm$^{-1}$ | 2950 | 2960 | 2950 |
| | 1740 | 1710 | 1720 |
| | 1460 | 1600 | 1455 |
| | 1170 | 1450 | 1270 |
| | 1100 | 1275 | 1180 |
| | | 1110 | 1110 |
| | | 710 | 715 |

The above triesters and comparative prior art esters were then incorporated into PVC by mixing 39 grams of PVC, 26 grams of triester and 0.65 gram of a commercial barium/cadmium laurate stabilizer. Mixing was accomplished by working the mixture on a rubber mill for 10 minutes at 310° to 320°F. The resulting sheets were then molded (using a conventional PVC mold) into film sheets 4 inches × 4 inches, in either 10-mil or 70-mil thicknesses. Molding temperature was 330°F. These films were then tested by the methods described in "Plasticizers: Paraplex and Monoplex", Rohm and Haas Co., 1960, pp. 84–89. The following tests were carried out:

1. Volatility — The details of the test are given in the above reference at page 84. In general, the weight loss of a PVC film containing a plasticizer at 90°C. for 24 hours is measured and reported as percent weight loss.

2. Soapy Water Extraction — The details of this test are in the above publication, pp. 85–86. In general, the weight loss of a plasticized PVC sample immersed in a 1% aqueous soap solution at 90°C. for 24 hours is measured and reported as percent weight loss.

3. Hexane Extraction — The details of the test method are given in the above-cited reference, page 86. In general, the loss in weight of a PVC film containing a plasticizer is determined after 2 hours' immersion in n-hexane at 25°C.

4. Hardness: A slightly modified Shore Durometer Hardness Test, as described on page 87 of the reference, was utilized. In this test, the initial value (0 sec.) of the hardness of a 70-mil sheet is determined using the Shore Durometer with a 2-pound (A) loading.

5. Flex ($T_F$) Temperature: This test was carried out by the well-known method of Clash and Berg (Ind. & Eng. Chem. 34, 1218 (1942). In this test, the angular twist of a rectangular test specimen is determined by applying a controlled torque of 5.68 × 10$^3$ dyne-cm to the sample 5 seconds after exposure to various low test temperatures. The temperature at which the angular twist is 200° of arc is then taken as the "flex" ($T_F$) temperature. Flex temperature is defined as "the lower temperature limit of the compound's usefulness as an elastomer".

The results of the above tests on PVC containing representative examples of the triesters of the present invention are given in Table II.

TABLE II
PLASTICIZER TEST RESULTS*

| Test No. | Plasticizer Incorporated | Volatility Loss, % | Soapy H₂O Loss, % | Hexane Loss, % | Hardness Shore A | Flex Temp. °C. |
|---|---|---|---|---|---|---|
| 1 | Triethanolmethanetri-2-ethylhexanoate | 2.0 | 7.5 | 37.5 | 82 | −49 |
| 2 | Triethanolmethanetrihexanoate | 5.3 | 26.6 | 27.3 | 75 | −53 |
| 3 | Triethanolmethanetribenzoate | 1.7 | 15.5 | 0.6 | 88 | 0 |
| 4 | Triethanolmethanedi-2-ethylhexanoate-benzoate | 3.1 | 15.7 | 16.2 | 81 | −28 |
| 5 | Dioctylphthalate** | 14.4 | 13.1 | 33.0 | 75 | −33 |
| 6 | Tri-2-ethylhexyltrimellitate** | 0.7 | (0.4)*** | 36.0 | 81 | −27 |
| 7 | Trimethylolpropanetri-2-ethylhexanoate | 9.1 | 14.4 | 37.7 | 90 | −27 |
| 8 | Trimethylolpropanetrihexanoate | 19.0 | 24.1 | 38.5 | 76 | −43 |
| 9 | Trimethylolpropanetribenzoate | 2.5 | 13.8 | 0.2 | 95 | +12 |
| 10 | Trimethylolpropanedi-2-ethylhexanoate-monobenzoate | | | Incompatible | | |

*All values are the averages of duplicate tests
**Commercial plasticizers
***Weight increase The results given in Table II show that the triesters of the present invention have excellent plasticizing properties. Especially important are the "flex" temperatures, which are surprisingly low when compared with the "flex" temperatures of the corresponding trimethylolpropane triesters (runs 1, 2, 3 and 4 compared to runs 7, 8, 9 and 10, respectively).

The structure of trimethanolpropane is very close to that of triethanolmethane, as shown below:

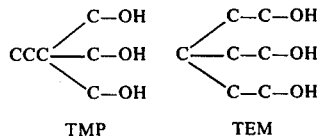

TMP        TEM

Plasticizers No. 1 or No. 2 in accordance with the present invention, that is, triester No. 1 (triethanolmethanetri-2-ethylhexanoate) or No. 2 (triethanolmethanetrihexanoate) given in Table II compared to the widely used prior art ester (dioctylphthalate), No. 5 in Table II, shows that triesters Nos. 1 and 2, in accordance with the present invention, afford a marked advantage as plasticizers over the commercially used dioctylphthalate. Also, the No. 3 triester (triethanolmethanetribenzoate) compared to No. 9 (trimethylolpropanetribenzoate) shows that the triester in accordance with the present invention, prepared using TEM, has an especially low flex temperature compared to the homolog compound which was made from trimethylolpropane instead of TEM. Thus, even though the No. 3 item of Table II did not have an especially low flex temperature, it did have an unexpectedly better flex temperature than did the corresponding homolog, No. 9, the latter being outside the scope of the present invention.

The triesters of triethanolmethane are also useful as synthetic lubricants. In conventional viscosity tests, the triesters of this invention have superior viscosity index (V.I.) values as compared to the corresponding trieters of trimethylolpropane. These results are presented in Table III.

TABLE III
TRIESTER VISCOSITY AND V.I.

| Run No. | Triester Tested | Viscosity (cstks) 100°F. | 210°F. | V.I. |
|---|---|---|---|---|
| 1 | Triethanolmethanetri-2-ethylhexanoate | 24.35 | 4.29 | 84 |
| 2 | Triethanolmethane-trihexanoate | 12.10 | 3.178 | 143 |
| 3 | Trimethylolpropanetri-2-ethylhexanoate | 33.62 | 4.648 | 28 |
| 4 | Trimethylolpropanetri-hexanoate | 13.68 | 3.139 | 100 |

What is claimed is:

1. A triester of the following formula:

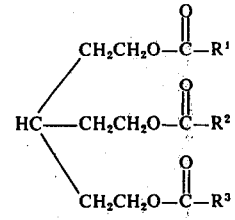

wherein R¹, R² and R³ are alkyl or hydrocarbyl aryl groups having from 2 to 14 carbon atoms.

2. A composition in accordance with claim 1, wherein R¹, R² and R³ are aryl or alkyl groups of 6 to 8 carbon atoms.

3. A composition in accordance with claim 1 wherein R¹, R² and R³ are alkyl groups of 6 to 8 carbon atoms.

4. Triethanolmethanetri-2-ethylhexanoate.

5. Triethanolmethanetrihexanoate.

* * * * *